United States Patent
Akahori

(10) Patent No.: US 11,244,455 B2
(45) Date of Patent: Feb. 8, 2022

(54) APPARATUS, METHOD, AND PROGRAM FOR TRAINING DISCRIMINATOR DISCRIMINATING DISEASE REGION, DISCRIMINATOR DISCRIMINATING DISEASE REGION, DISEASE REGION DISCRIMINATION APPARATUS, AND DISEASE REGION DISCRIMINATION PROGRAM

(71) Applicant: FUJIFILM Corporation, Tokyo (JP)

(72) Inventor: Sadato Akahori, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 65 days.

(21) Appl. No.: 16/584,847

(22) Filed: Sep. 26, 2019

(65) Prior Publication Data

US 2020/0104996 A1    Apr. 2, 2020

(30) Foreign Application Priority Data

Oct. 1, 2018 (JP) .............................. JP2018-186789

(51) Int. Cl.
*G06K 9/00* (2006.01)
*G06T 7/00* (2017.01)
(Continued)

(52) U.S. Cl.
CPC ........... *G06T 7/0014* (2013.01); *G16H 30/40* (2018.01); *G16H 50/20* (2018.01);
(Continued)

(58) Field of Classification Search
CPC ....... G06T 2200/04; G06T 2207/10081; G06T 2207/20081; G06T 2207/20084;
(Continued)

(56) References Cited

U.S. PATENT DOCUMENTS

2018/0218503 A1* 8/2018 Xu ........................... G06N 3/04
2019/0005684 A1* 1/2019 De Fauw ............. G06K 9/6262
(Continued)

FOREIGN PATENT DOCUMENTS

JP    H08-251404    9/1996

OTHER PUBLICATIONS

Shuai Xiao, Joint Modeling of Event Sequence and Time Series with Attentional Twin Recurrent Neural Networks, May 24, 2017 V1, IEEE.*

(Continued)

*Primary Examiner* — Xin Jia
(74) *Attorney, Agent, or Firm* — JCIPRNET

(57) ABSTRACT

A discriminator includes a common learning unit and a plurality of learning units that are connected to an output unit of the common learning unit. The discriminator is trained, using a plurality of data sets of a medical image and an image data of a first disease region, such that information indicating the first disease region is output from a first learning unit in a case in which the medical image is input to the common learning unit. The discriminator is trained, using a plurality of data sets of a medical image and an image data of a second disease region having at least one of a medical causal relationship or an anatomic causal relationship with the first disease, such that information indicating the second disease region is output from a second learning unit in a case in which the medical image is input to the common learning unit.

20 Claims, 11 Drawing Sheets

(51) Int. Cl.
　　　*G16H 30/40*　　　(2018.01)
　　　*G16H 50/20*　　　(2018.01)
(52) U.S. Cl.
　　　CPC .............. *G06T 2207/10081* (2013.01); *G06T 2207/20081* (2013.01); *G06T 2207/30016* (2013.01)
(58) Field of Classification Search
　　　CPC ......... G06T 2207/30016; G06T 7/0012; G06T 7/0014; G16H 30/40; G16H 40/20; G16H 50/20
　　　See application file for complete search history.

(56) References Cited

U.S. PATENT DOCUMENTS

2020/0020098 A1\* 1/2020 Odry .................... G06K 9/6245
2020/0085290 A1\* 3/2020 Wang ....................... A61B 3/12

OTHER PUBLICATIONS

Google Scholar Search Record.\*

\* cited by examiner

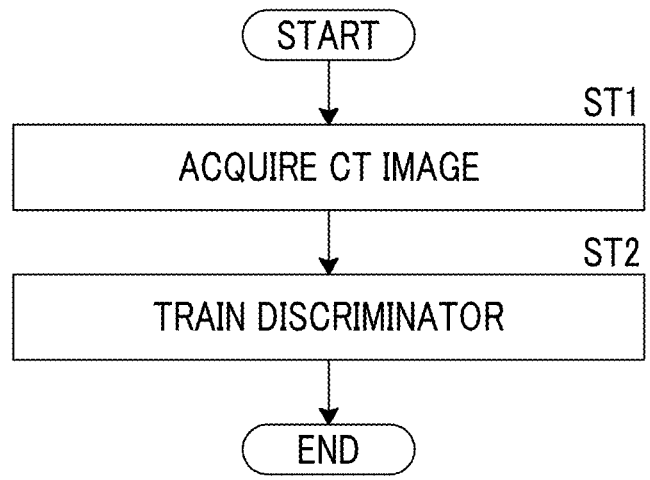
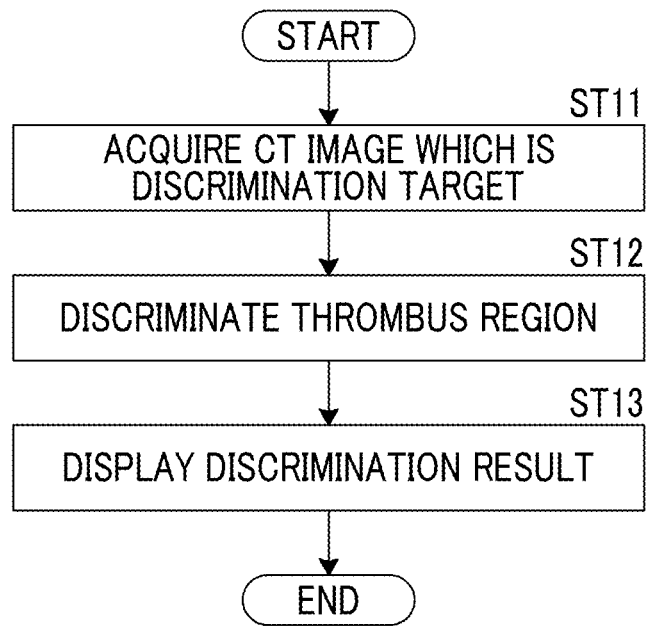

APPARATUS, METHOD, AND PROGRAM FOR TRAINING DISCRIMINATOR DISCRIMINATING DISEASE REGION, DISCRIMINATOR DISCRIMINATING DISEASE REGION, DISEASE REGION DISCRIMINATION APPARATUS, AND DISEASE REGION DISCRIMINATION PROGRAM

CROSS-REFERENCE TO RELATED APPLICATIONS

The present application claims priority under 35 U.S.C. § 119 to Japanese Patent Application No. 2018-186789, filed on Oct. 1, 2018. Each of the above application is hereby expressly incorporated by reference, in its entirety, into the present application.

BACKGROUND OF THE INVENTION

1. Field of the Invention

The present disclosure relates to an apparatus, method, and a non-transitory computer readable medium for storing program for training a discriminator discriminating a disease region, a discriminator discriminating a disease region, a disease region discrimination apparatus, and a a non-transitory computer readable medium for storing disease region discrimination program.

2. Description of the Related Art

In recent years, advances in medical apparatuses, such as a computed tomography (CT) apparatus and a magnetic resonance imaging (MRI) apparatus, have made it possible to perform image diagnosis using high-resolution medical images with higher quality. In particular, in a case in which a target part is the brain, image diagnosis using, for example, CT images and MRI images makes it possible to specify disease regions causing cerebrovascular disorders, such as cerebral infarction, cerebral thrombosis, and cerebral hemorrhage. Therefore, appropriate treatment is performed on the basis of the specification results.

Various methods for automatically discriminating a disease region from a medical image have been proposed. For example, JP1996-251404A (JP-H08-251404A) discloses a discrimination apparatus that comprises first and second neural networks each of which includes an input layer, an intermediate layer, and an output layer and which are connected to each other such that an output from the input layer to the intermediate layer in the first neural network is input to the input layer of the second neural network. In the discrimination apparatus disclosed in JP1996-251404A (JP-H08-251404A), the discrimination result of a region attribute of image data is output on the basis of the image data input to the first neural network. The use of the discrimination apparatus makes it possible to discriminate specific medical characteristics included in the above-mentioned medical image.

SUMMARY OF THE INVENTION

A thrombus region extracted from a CT image provides a clue to specify an acute infarction. In addition, the specification of the thrombus region is also required for endovascular treatment. However, it is difficult to see the blood vessels on a non-contrast-enhanced CT image since the blood vessels are not contrasted. Therefore, the thrombus region is not always clear and it is difficult to specify the position of the thrombus region. For this reason, it is desirable to automatically extract the thrombus region using a computer. Deep learning which has attracted attention in recent years can be applied as a method for automatically extracting the thrombus region. However, learning information including a plurality of data sets of CT images and correct thrombus regions in the CT images is required for deep learning. However, since the thrombus region is not always clear on the CT image as described above, it is difficult to prepare a large amount of data indicating the correct thrombus region in the CT image.

The present disclosure has been made in view of the above-mentioned problems and an object of the present disclosure is to provide a technique that discriminates a disease region with high accuracy, using a limited amount of data, even in an image in which it is difficult to prepare a large amount of data indicating a correct disease region.

According to the present disclosure, there is provided a learning method that trains a discriminator comprising a common learning unit that includes an input unit and an output unit and a plurality of learning units each of which includes an input unit which is connected to the output unit of the common learning unit and an output unit. The learning method comprises: training the discriminator, using a plurality of data sets of a medical image and a correct mask of a first disease region in which a first disease appears in the medical image, such that information indicating the first disease region is output from the output unit of a first learning unit among the plurality of learning units in a case in which the medical image is input to the input unit of the common learning unit; and training the discriminator, using a plurality of data sets of a medical image and a correct mask of a second disease region in which a second disease having at least one of a medical causal relationship or an anatomic causal relationship with the first disease appears in the medical image, such that information indicating the second disease region is output from the output unit of a second learning unit among the plurality of learning units in a case in which the medical image is input to the input unit of the common learning unit.

In the learning method according to the present disclosure, the discriminator may be trained, using a plurality of data sets of a medical image and correct information of an anatomic part of the first disease in the medical image, such that information indicating the anatomic part of the first disease is output from the output unit of a third learning unit among the plurality of learning units in a case in which the medical image is input to the input unit of the common learning unit.

In the learning method according to the present disclosure, the discriminator may be trained, using a plurality of data sets of a medical image and information indicating whether or not the second disease is present in the medical image, such that the information indicating whether or not the second disease is present is output from the output unit of a fourth learning unit among the plurality of learning units in a case in which the medical image is input to the input unit of the common learning unit.

In the learning method according to the present disclosure, each of the common learning unit and the plurality of learning units may be a neural network that comprises an input layer as the input unit, a plurality of intermediate layers, and an output layer as the output unit.

In the learning method according to the present disclosure, the first disease may be thrombus and the second disease may be infarction.

In the learning method according to the present disclosure, the medical image may be a brain image.

In addition, a non-transitory computer readable medium for storing a program that causes a computer to perform the learning method according to the present disclosure may be provided.

According to the present disclosure, there is provided a learning apparatus that trains a discriminator comprising a common learning unit that includes an input unit and an output unit and a plurality of learning units each of which includes an input unit which is connected to the output unit of the common learning unit and an output unit. The learning apparatus trains the discriminator, using a plurality of data sets of a medical image and a correct mask of a first disease region in which a first disease appears in the medical image, such that information indicating the first disease region is output from the output unit of a first learning unit among the plurality of learning units in a case in which the medical image is input to the input unit of the common learning unit. In addition, the learning apparatus trains the discriminator, using a plurality of data sets of a medical image and a correct mask of a second disease region in which a second disease having at least one of a medical causal relationship or an anatomic causal relationship with the first disease appears in the medical image, such that information indicating the second disease region is output from the output unit of a second learning unit among the plurality of learning units in a case in which the medical image is input to the input unit of the common learning unit.

Another learning apparatus according to the present disclosure trains a discriminator comprising a common learning unit that includes an input unit and an output unit and a plurality of learning units each of which includes an input unit which is connected to the output unit of the common learning unit and an output unit and comprises a memory that stores commands executed by a computer and a processor that is configured to execute the stored commands. The processor performs a process of training the discriminator, using a plurality of data sets of a medical image and a correct mask of a first disease region in which a first disease appears in the medical image, such that information indicating the first disease region is output from the output unit of a first learning unit among the plurality of learning units in a case in which the medical image is input to the input unit of the common learning unit. In addition, the processor performs a process of training the discriminator, using a plurality of data sets of a medical image and a correct mask of a second disease region in which a second disease having at least one of a medical causal relationship or an anatomic causal relationship with the first disease appears in the medical image, such that information indicating the second disease region is output from the output unit of a second learning unit among the plurality of learning units in a case in which the medical image is input to the input unit of the common learning unit.

According to the present disclosure, there is provided a discriminator that is trained by any one of the learning method, the learning apparatus, or the non-transitory computer readable medium for storing learning program according to the present disclosure.

According to the present disclosure, there is provided a disease region discrimination apparatus comprising: an image acquisition unit that acquires a medical image which is a discrimination target; and the discriminator according to the present disclosure that discriminates a first disease region in the medical image which is the discrimination target.

Another disease region discrimination apparatus according to the present disclosure comprises: an image acquisition unit that acquires a medical image which is a discrimination target; and the discriminator according to the present disclosure that discriminates a second disease region in the medical image which is the discrimination target.

The disease region discrimination apparatus according to the present disclosure may further comprise a display control unit that displays a discrimination result of the discriminator on a display unit.

According to the present disclosure, there is provided a non-transitory computer readable medium for storing a disease region discrimination program that causes a computer to perform: a process of acquiring a medical image which is a discrimination target; and a process of allowing the discriminator according to the present disclosure to discriminate a first disease region in the medical image which is the discrimination target.

Another non-transitory computer readable medium for storing disease region discrimination program according to the present disclosure causes a computer to perform: a process of acquiring a medical image which is a discrimination target; and a process of allowing the discriminator according to the present disclosure to discriminate a second disease region in the medical image which is the discrimination target.

Still another disease region discrimination apparatus according to the present disclosure comprises a memory that stores commands executed by a computer and a processor that is configured to execute the stored commands. The processor performs: a process of acquiring a medical image which is a discrimination target; and a process of allowing the discriminator according to the present disclosure to discriminate a first disease region in the medical image which is the discrimination target.

Yet another disease region discrimination apparatus according to the present disclosure comprises a memory that stores commands executed by a computer and a processor that is configured to execute the stored commands. The processor performs: a process of acquiring a medical image which is a discrimination target; and a process of allowing the discriminator according to the present disclosure to discriminate a second disease region in the medical image which is the discrimination target.

According to the apparatus, method, and non-transitory computer readable medium for storing program for training a discriminator discriminating a disease region, the discriminator discriminating a disease region, the disease region discrimination apparatus, and non-transitory computer readable medium for storing disease region discrimination program of the present disclosure, it is possible to discriminate a disease region, using a limited amount of data, even in an image in which it is difficult to prepare a large amount of data indicating a correct disease region.

BRIEF DESCRIPTION OF THE DRAWINGS

FIG. 8 is a flowchart illustrating a process performed during learning in the first embodiment.

FIG. 9 is a flowchart illustrating a process performed during the discrimination of a thrombus region.

DESCRIPTION OF THE PREFERRED EMBODIMENTS

Figure 1:
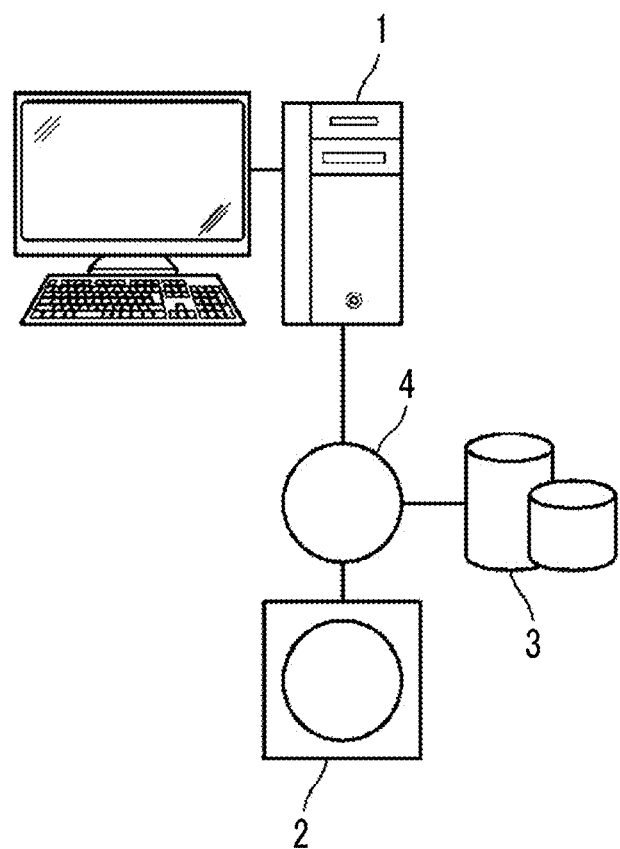
FIG. 1 is a hardware configuration diagram illustrating the outline of a diagnosis support system to which a disease region discrimination apparatus according to an embodiment of the present disclosure is applied.

Hereinafter, a first embodiment of the present disclosure will be described with reference to the drawings. FIG. 1 is a hardware configuration diagram illustrating the outline of a diagnosis support system to which a learning apparatus for training a discriminator, a discriminator, and a disease region discrimination apparatus according to an embodiment of the present disclosure are applied. As illustrated in FIG. 1, in the diagnosis support system, a disease region discrimination apparatus 1, a three-dimensional imaging apparatus 2, and an image storage server 3 according to this embodiment are connected so as to communicate with each other through a network 4. In addition, the disease region discrimination apparatus 1 includes the learning apparatus and the discriminator according to this embodiment.

The three-dimensional imaging apparatus 2 captures an image of a part of a subject to be diagnosed and generates a three-dimensional image indicating the part. Specifically, the three-dimensional imaging apparatus 2 is, for example, a CT apparatus, an MRI apparatus, or a PET apparatus. A medical image generated by the three-dimensional imaging apparatus 2 is transmitted to the image storage server 3 and is then stored therein. In this embodiment, a diagnosis target part of a patient that is the subject is the brain and the three-dimensional imaging apparatus 2 is a CT apparatus. The CT apparatus 2 generates a three-dimensional CT image B0 including the brain of the subject. In this embodiment, the CT image B0 is a non-contrast-enhanced CT image acquired by imaging without using a contrast medium. However, a contrast-enhanced CT image acquired by imaging using a contrast medium may be used.

The image storage server 3 is a computer that stores and manages various types of data and comprises a high-capacity external storage device and database management software. The image storage server 3 performs communication with other apparatuses through the wired or wireless network 4 to transmit and receive, for example, image data. Specifically, the image storage server 3 acquires various types of data including image data of the CT image generated by the three-dimensional imaging apparatus 2 through the network, stores the acquired data in a recording medium, such as a high-capacity external storage device, and manages the data. In addition, the storage format of the image data and the communication between the apparatuses through the network 4 are based on a protocol such as Digital Imaging and Communication in Medicine (DICOM).

The disease region discrimination apparatus 1 is configured by installing a learning program and a disease region discrimination program according to the present disclosure in one computer. The computer may be a workstation or a personal computer that is directly operated by a doctor who performs diagnosis or may be a server computer that is connected with them through the network. The learning program and the disease region discrimination program are recorded on a recording medium, such as a digital versatile disc (DVD) or a compact disc read only memory (CD-ROM), and are then distributed. The learning program and the disease region discrimination program are installed in the computer from the recording medium. Alternatively, the learning program and the disease region discrimination program are stored in a storage device of a server computer connected to the network or a network storage so as to be accessed from the outside, are downloaded to the computer used by the doctor on request, and are then installed in the computer.

Figure 2:
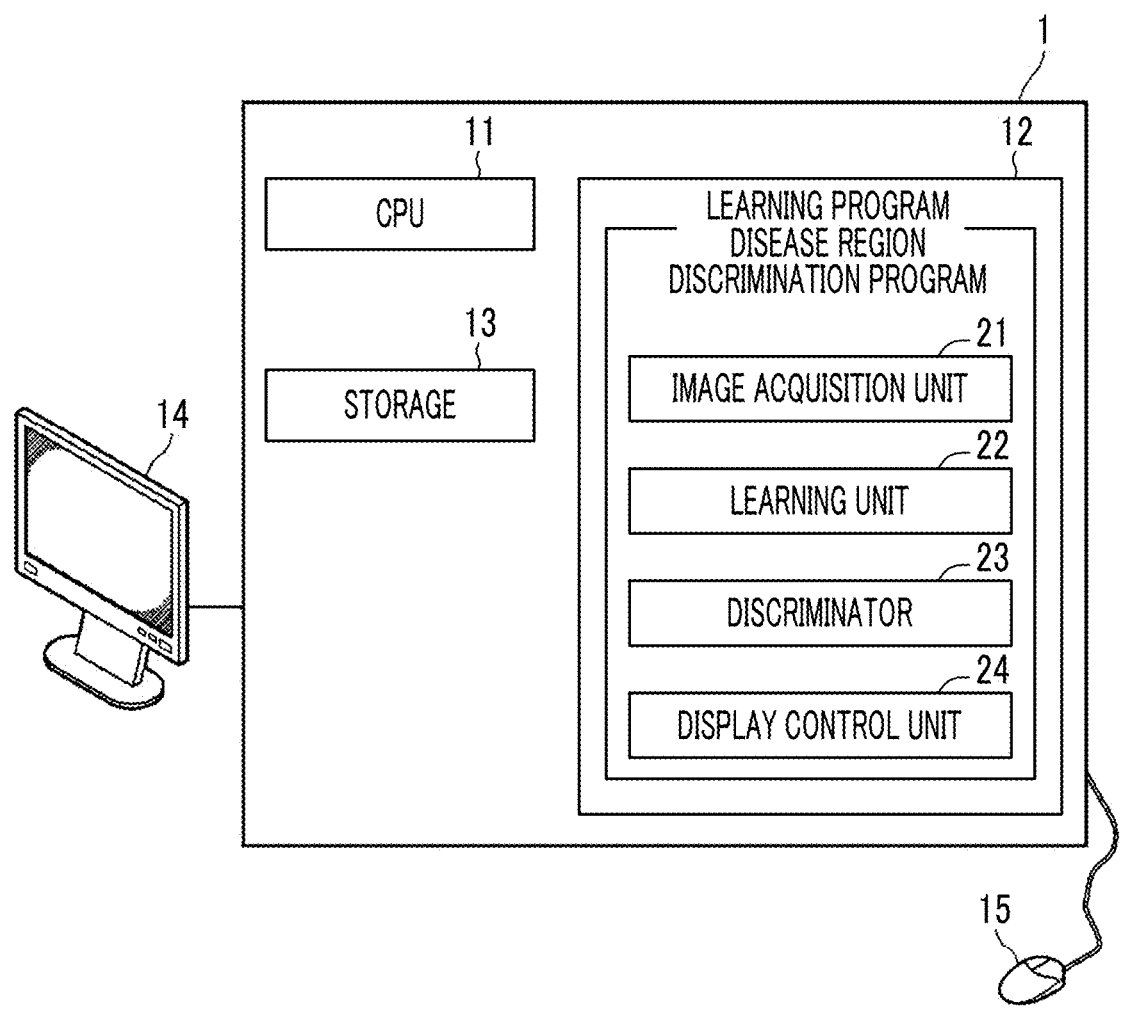
FIG. 2 is a block diagram schematically illustrating the configuration of the disease region discrimination apparatus according to a first embodiment of the present disclosure.

FIG. 2 is a diagram schematically illustrating the configuration of the disease region discrimination apparatus according to the embodiment of the present disclosure which is implemented by installing the learning program and the disease region discrimination program in the computer. As illustrated in FIG. 2, the disease region discrimination apparatus 1 has the configuration of a standard workstation and comprises a central processing unit (CPU) 11, a memory 12, and a storage 13. In addition, a display unit 14, such as a liquid crystal display, and an input unit 15 including, for example, a keyboard and a mouse are connected to the disease region discrimination apparatus 1. The input unit 15 receives various setting inputs from the user. In addition, a touch panel may be used so as to function as both the display unit 14 and the input unit 15.

The storage 13 is, for example, a hard disk drive or a solid state drive (SSD). The storage 13 stores various kinds of information including the medical images of the subject and information required for processes which are acquired from the image storage server 3 through the network 4.

The memory 12 stores the learning program and the disease region discrimination program. The learning program is used to train a discriminator 23 comprising a first convolutional neural network (CNN) 31 (common learning unit) which will be described below, a second CNN 32 (first learning unit) which will be described below, and a third CNN 33 (second learning unit) which will be described below and defines, as the processes performed by the CPU 11, the following processes: a process which trains the discriminator, using a plurality of data sets of a CT image and a correct mask of a thrombus region in which thrombus appears in the CT image, such that information indicating the thrombus region is output from an output unit of the second CNN 32 in a case in which the CT image is input to an input unit of the first CNN 31; and a process which trains the discriminator, using a plurality of data sets of a CT image and a correct mask of an infarction region in which infarction appears in the CT image, such that information indicating the infarction region is output from an output unit of the third CNN 33 in a case in which the CT image is input to the input unit of the first CNN 31. A correct mask is an image data that defines a disease region in which a disease appears in a medical image and a disease region is specified in a medical image. A correct mask is, for example, an image data having a pixel value of 1 for pixels in a disease region and a pixel value of 0 for pixels in the region other than a disease region.

In addition, the disease region discrimination program defines, as the processes performed by the CPU 11, the following processes: an image acquisition process that acquires a CT image which is a discrimination target; a discrimination process that discriminates a thrombus region or an infarction region in the CT image which is a discrimination target; and a display control process that displays the discrimination result of the discriminator 23 on the display unit 14.

Then, the CPU 11 performs these processes according to the program such that the computer functions as an image acquisition unit 21, a learning unit 22, the discriminator 23, and a display control unit 24. Here, the learning unit 22 forms the learning apparatus for training the discriminator 23 according to this embodiment. In addition, the image acquisition unit 21, the discriminator 23, and the display control unit 24 form the disease region discrimination apparatus according to this embodiment.

The image acquisition unit 21 acquires a CT image Bt1 of the brain of the subject that has developed cerebral thrombosis and a CT image Bi1 of the brain of the subject that has developed cerebral infarction from the image storage server 3 in order to train the discriminator 23 which will be described below. In addition, the image acquisition unit 21 acquires the CT image B0, from which disease regions are to be extracted, from the image storage server 3 in order to extract the disease regions such as a thrombus region and an infarction region. In addition, in a case in which the CT image Bt1, the CT image Bi1, and the CT image B0 have been stored in the storage 13, the image acquisition unit 21 may acquire the CT image Bt1, the CT image Bi1, and the CT image B0 from the storage 13. Further, the image acquisition unit 21 acquires the CT images Bt1 and the CT images Bi1 of a large number of subjects in order to train the discriminator 23 which will be described below.

Figure 3:
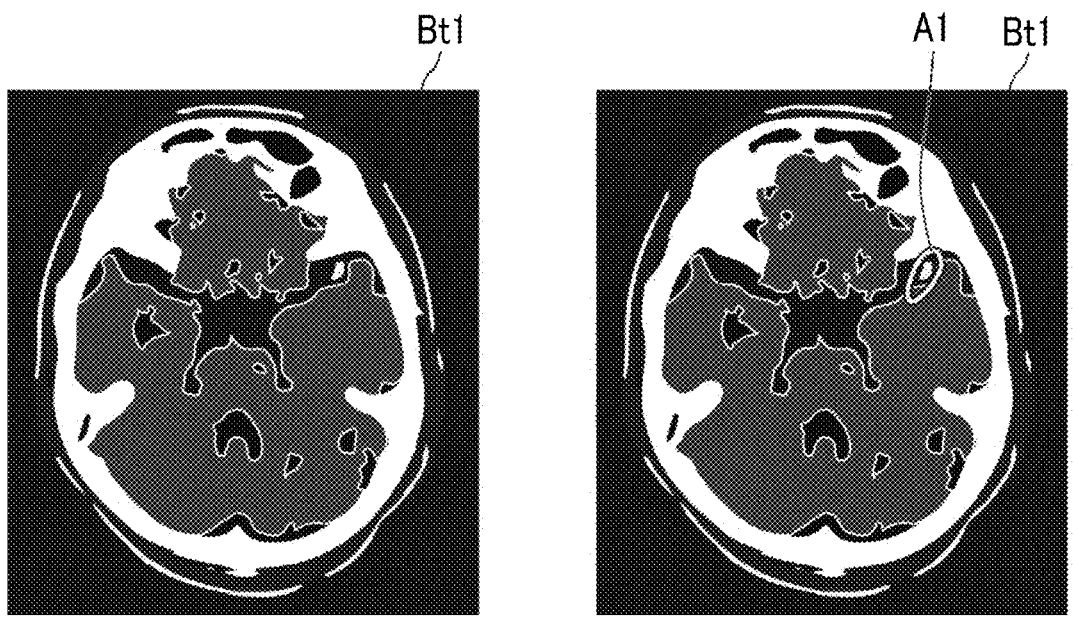
FIG. 3 is a diagram illustrating a data set of a CT image and a thrombus region.
Figure 4:
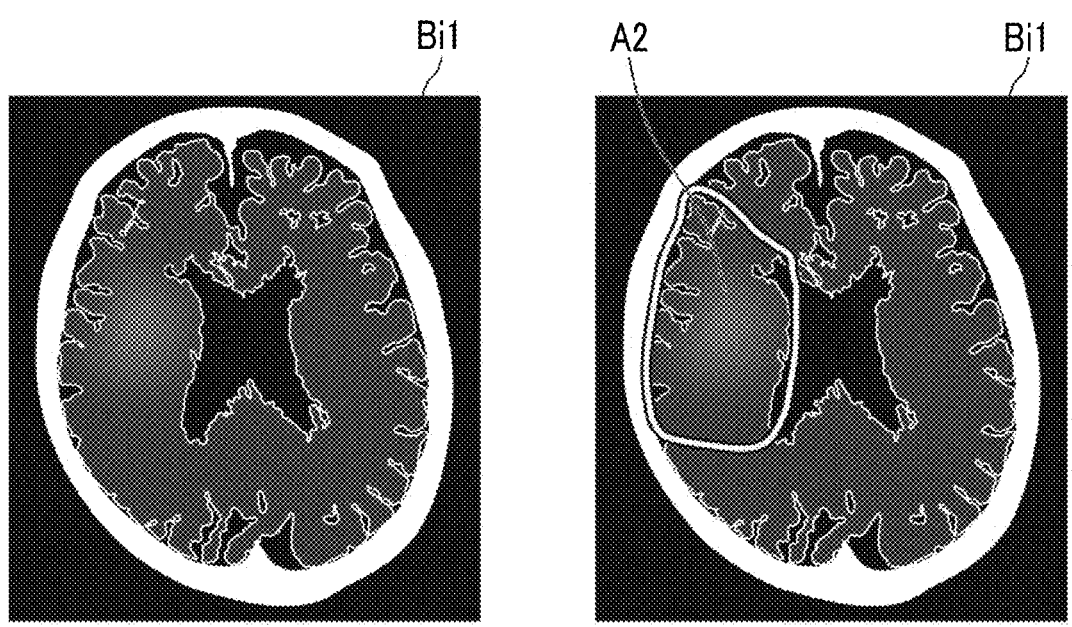
FIG. 4 is a diagram illustrating a data set of a CT image and an infarction region.

The learning unit 22 trains the discriminator 23. FIG. 3 is a diagram illustrating an example of the CT image Bt1 and a thrombus region A1 and FIG. 4 is a diagram illustrating an example of a data set of the CT image Bi1 and an infarction region A2. The learning unit 22 trains the discriminator 23 that discriminates the thrombus region in the input CT image B0, using the data set of the CT image Bt1 and the thrombus region A1 specified in the CT image Bt1 as training data, as illustrated in FIG. 3. In addition, the learning unit 22 trains the discriminator 23 that discriminate the infarction region in the input CT image B0, using the data set of the CT image Bi1 and the infarction region A2 specified in the CT image Bi1 as training data, as illustrated in FIG. 4.

Here, the discriminator 23 will be described. The discriminator 23 discriminates a disease region in the CT image B0 of the brain. In this embodiment, the thrombus region and the infarction region are used as the disease regions. In this embodiment, it is assumed that the discriminator 23 includes a plurality of convolutional neural networks (hereinafter, referred to as CNNs) which are one of multi-layer neural networks that have a plurality of processing layers hierarchically connected to each other and are subjected to deep learning.

Figure 5:
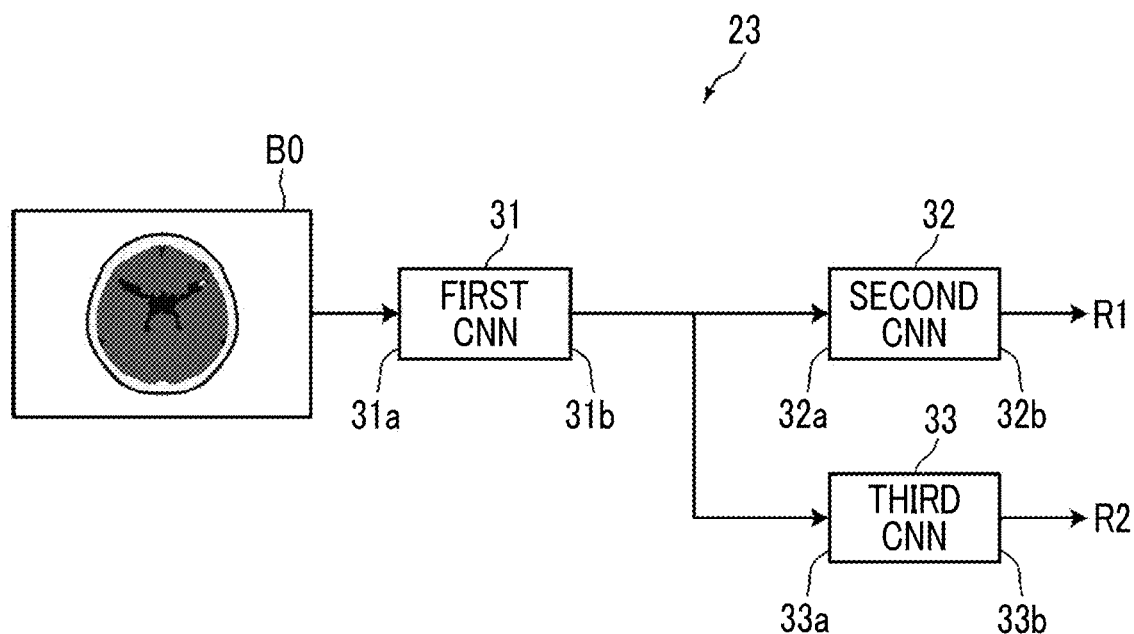
FIG. 5 is a diagram schematically illustrating the configuration of a discriminator in the first embodiment.

FIG. 5 is a diagram schematically illustrating the configuration of the discriminator 23 in this embodiment. As illustrated in FIG. 5, the discriminator 23 includes the first CNN 31, the second CNN 32, and the third CNN 33. The first CNN 31, the second CNN 32, and the third CNN 33 are configured to have a plurality of processing layers including input layers 31a, 32a, and 33a as input units and output layers 31b, 32b, and 33b as output units, respectively. The output layer 31b of the first CNN 31 is connected to the input layer 32a of the second CNN 32 and the input layer 33a of the third CNN 33. The first CNN 31 corresponds to a common learning unit according to the present disclosure, the second CNN 32 corresponds to a first learning unit according to the present disclosure, and the third CNN 33 corresponds to a second learning unit according to the present disclosure.

The processing layers of the first CNN 31, the second CNN 32, and the third CNN 33 include at least one of a convolutional layer or a pooling layer. The convolutional layer performs a convolution process using various kernels for an input image and outputs a feature amount map including feature amount data obtained by the convolution process. The kernel has a size of n×n pixels (for example, n=3) and a weight is set to each element. Specifically, a weight, such as a differential filter that enhances the edge of a two-dimensional image, such as the CT image B0 of the brain or a feature amount map, is set. The convolutional layer applies the kernel to the entire CT image B0 of the brain or the entire feature amount map while shifting the pixel of interest of the kernel. In addition, the convolutional layer applies an activation function, such as a sigmoid function, to the value subjected to convolution and outputs a feature amount map.

The pooling layer pools the feature amount map output from the convolutional layer to reduce the amount of data of the feature amount map and outputs the feature amount map whose amount of data has been reduced.

In this embodiment, the convolution process using a two-dimensional kernel is used. However, the technology according to the present disclosure is not limited thereto. For example, a convolution process using a three-dimensional filter may be used. For example, in a case in which a three-dimensional kernel is used, the kernel has a size of n×n×n voxels (for example, n=3) and a weight is set to each element.

In this embodiment, the first CNN 31 and the second CNN 32 are trained, using a data set of a plurality of CT images of the brain including a thrombus region and the thrombus region specified in the CT images as training data, so as to output a discrimination result R1 of the thrombus region for each pixel included in the input CT image. The thrombus region corresponds to a first disease. In a case in which the CT image B0 is input to the input layer 31a of the first CNN 31, among a plurality of processing layers of the first CNN 31 and the second CNN 32, a feature amount map output from a processing layer in the previous stage is sequentially input to a processing layer in the next stage and the discrimination result R1 of the thrombus region for each pixel of the CT image B0 is output from the output layer 32b of the second CNN 32. In addition, the discrimination result R1 output from the second CNN 32 is the result of discriminating whether each pixel of the CT image B0 is a thrombus region or a region other than the thrombus region.

In addition, the first CNN 31 and the third CNN 33 are trained, using a data set of a plurality of CT images of the brain including an infarction region and the infarction region specified in the CT images as training data, so as to output a discrimination result R2 of the infarction region for each pixel included in the input CT image. The infarction region corresponds to a second disease. In a case in which the CT image B0 is input to the input layer 31a of the first CNN 31, among a plurality of processing layers of the first CNN 31 and the third CNN 33, a feature amount map output from a processing layer in the previous stage is sequentially input to a processing layer in the next stage and the discrimination result R2 of the infarction region for each pixel of the CT image B0 is output from the output layer 33b of the third CNN 33. In addition, the discrimination result R2 output from the third CNN 33 is the result of discriminating whether each pixel of the CT image B0 is an infarction region or a region other than the infarction region.

Here, in this embodiment, the feature amount map output from the output layer 31b of the first CNN 31 is input to both the input layer 32a of the second CNN 32 and the input layer 33a of the third CNN 33. That is, the first CNN 31 outputs the feature amount map common to a case in which the thrombus region is discriminated and a case in which the infarction region is discriminated. In this embodiment, the output layer 31b of the first CNN 31 outputs the feature amount map. However the output layer 31b may output a feature amount data of an input image. Here, the feature amount data is data that characterizes the input image and include a value calculated by a predetermined algorithm using one or more of luminance data, color data, edge information, etc. of the input image.

In general, in a case in which cerebral thrombosis is developed, oxygen and nutrients are not sent to the brain. Therefore, brain cells are damaged and cerebral infarction is developed. That is, there is a medical causal relationship between cerebral thrombosis and cerebral infarction and there is an anatomic causal relationship between the thrombus region and the infarction region. For this reason, the learning of the feature amount maps with training data for both cerebral thrombosis and cerebral infarction makes it possible to use image features found in cerebral infarction in a case in which a cerebral thrombosis region is extracted or image features found in cerebral thrombosis in a case in which a cerebral infarction region is extracted. Therefore, it is possible to improve accuracy by using image features that are related to each other. In this embodiment, the common feature amount map output from the output layer 31b of the first CNN 31 is input to the input layers 32a and 33a of the second and third CNNs 32 and 33. Then, the discrimination result R1 of the thrombus region in the CT image B0 is output from the output layer 32b of the second CNN 32 and the discrimination result R2 of the infarction region in the CT image B0 is output from the output layer 33b of the third CNN 33.

In some cases, in the CT image B0 obtained by non-contrast-enhanced CT, it is difficult to see the blood vessels on the image since the blood vessels are not contrasted. As a result, the thrombus region is not always clear and it may be difficult to specify the position of the thrombus region. Therefore, it is difficult to prepare a large amount of data indicating a correct thrombus region in the CT image B0. In this embodiment, the first CNN 31 is trained using not only data indicating a correct thrombus region but also data indicating a correct infarction region. That is, not only the knowledge of thrombus but also the knowledge of infarction is reflected in the discrimination result R1 of the thrombus region output from the second CNN 32. Therefore, the accuracy of the discrimination result is improved. Similarly, not only the knowledge of infarction but also the knowledge of thrombus is reflected in the discrimination result R2 of the infarction region output from the third CNN 33. Therefore, the accuracy of the discrimination result is improved. Therefore, in this embodiment, it is possible to discriminate a disease region with high accuracy using the limited amount of data even in an image in which it is difficult to prepare a large amount of data indicating a correct disease region.

Figure 6:
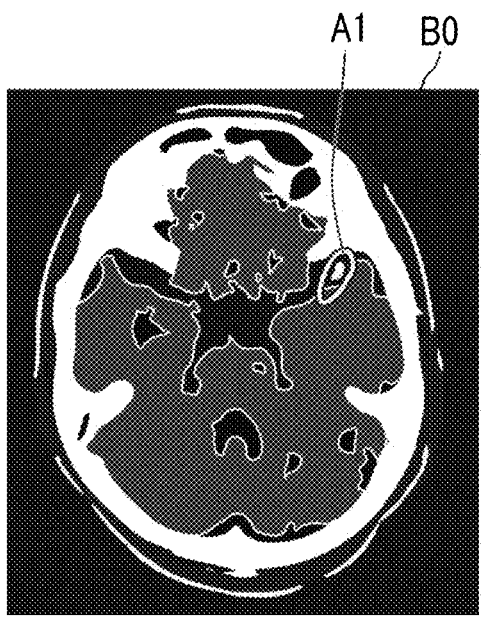
FIG. 6 is a diagram illustrating a displayed CT image of the brain.
Figure 7:
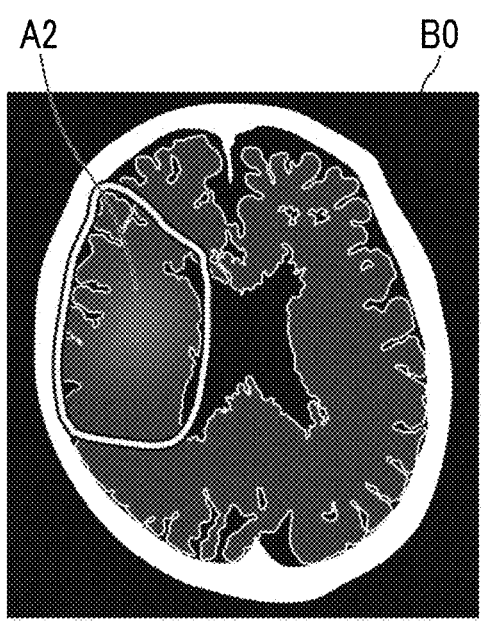
FIG. 7 is a diagram illustrating a displayed CT image of the brain.

The display control unit 24 displays the brain image in which the thrombus region and the infarction region have been discriminated on the display unit 14. FIGS. 6 and 7 are diagrams illustrating the displayed CT image of the brain. In addition, FIGS. 6 and 7 illustrate a slice image in one tomographic plane of the CT image B0. The thrombus region A1 discriminated in the CT image B0 is displayed so as to be surrounded by a line as illustrated in FIG. 6. In addition, the display control unit 24 may display the thrombus region A1 in any aspect on the display unit 14. For example, the display control unit 24 may display the thrombus region A1 so as to be hatched, may give a specific color to the thrombus region A1, may apply an arrow to the thrombus region A1, or may highlight the thrombus region A1 differently from other regions. The infarction region A2 discriminated in the CT image B0 is displayed so as to be surrounded by a line as illustrated in FIG. 7. In addition, the display control unit 24 may display the infarction region A2 in any aspect on the display unit 14. For example, the display control unit 24 may hatch the infarction region A2, may give a specific color to the infarction region A2, may apply an arrow to the infarction region A2, or may highlight the infarction region A2 differently from other regions.

Next, a process performed in this embodiment will be described. FIG. 8 is a flowchart illustrating a process performed during learning in this embodiment. First, the image acquisition unit 21 acquires the CT images Bt1 and Bi1 of the brain of the subject that has developed cerebral thrombosis or cerebral infarction (Step ST1). Then, the learning unit 22 trains the discriminator 23 that discriminates a thrombus region and an infarction region in the input CT image B0, using the thrombus region and the infarction region specified in the CT images Bt1 and Bi1 as training data (Step ST2). Then, the process ends.

FIG. 9 is a flowchart illustrating a process performed during the discrimination of the thrombus region in this embodiment. First, the image acquisition unit 21 acquires the CT image B0 which is a discrimination target (Step ST11) and the discriminator 23 discriminates the thrombus region in the CT image B0 which is a discrimination target (Step ST12). Then, the display control unit 24 displays the CT image B0 in which the thrombus region has been discriminated on the display unit 14 (Step ST13). Then, the process ends.

Figure 10:
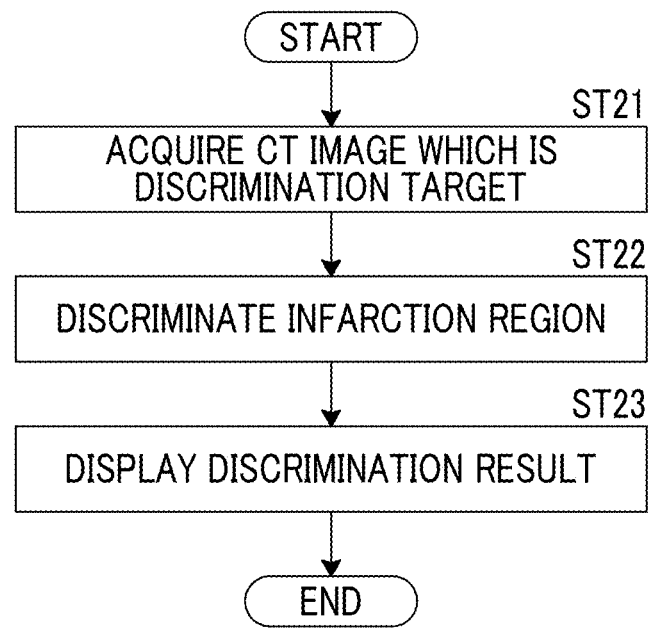
FIG. 10 is a flowchart illustrating a process performed during the discrimination of an infarction region.

FIG. 10 is a flowchart illustrating a process performed during the discrimination of an infarction region in this embodiment. First, the image acquisition unit 21 acquires the CT image B0 which is a discrimination target (Step ST21) and the discriminator 23 discriminates the infarction region in the CT image B0 which is a discrimination target (Step ST22). Then, the display control unit 24 displays the CT image B0 in which the infarction region has been discriminated on the display unit 14 (Step ST23). Then, the process ends.

As described above, in the first embodiment, not only the knowledge of thrombus but also the knowledge of infarction is reflected in the discrimination result of the thrombus region output from the second CNN 32. Similarly, not only the knowledge of infarction but also the knowledge of thrombus is reflected in the discrimination result of the infarction region output from the third CNN 33. As a result, the accuracy of the discrimination result is improved. Therefore, in this embodiment, it is possible to discriminate a disease region with high accuracy using the limited amount of data even in an image in which it is difficult to prepare a large amount of data indicating a correct disease region.

Next, a second embodiment of the present disclosure will be described with reference to the drawings. A disease region discrimination apparatus according to the second embodiment has substantially the same configuration as that according to the above-described embodiment. Therefore, here, the detailed description of the configuration of the disease region discrimination apparatus will not be repeated and only different portions will be described in detail.

Figure 11:
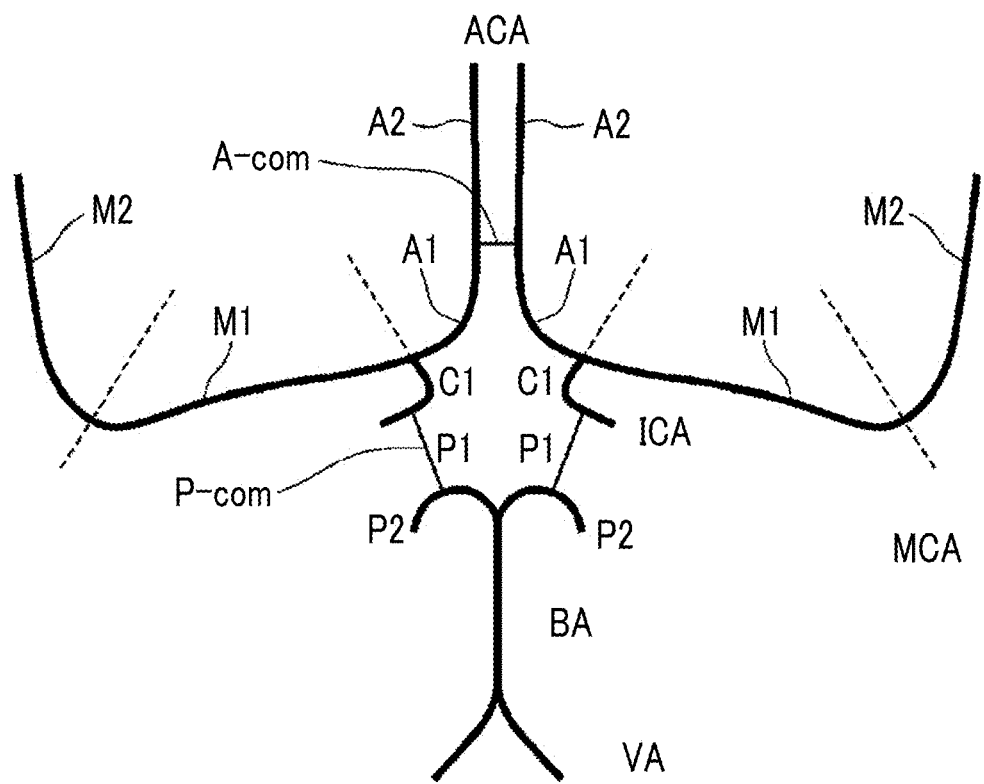
FIG. 11 is a diagram illustrating an anatomic part of the blood vessel of the brain.

A learning unit 22-2 according to the second embodiment trains a discriminator 23-2. FIG. 11 is a diagram illustrating an anatomic part of the brain blood vessel. For example, as illustrated in FIG. 11, the anatomic part includes the internal carotid artery (ICA), the anterior cerebral artery (ACA), the middle cerebral artery (MCA), and the posterior cerebral artery (PCA). In addition, a known anatomic part can be used as the anatomic part of the brain blood vessel.

Figure 12:
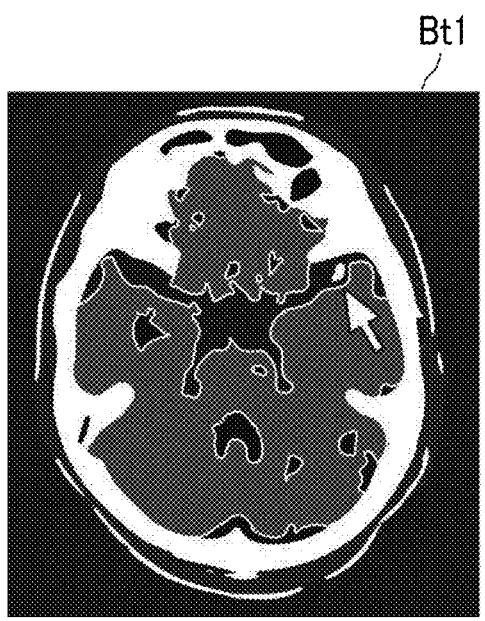
FIG. 12 is a diagram illustrating an example of the CT image of the brain.

FIG. 12 is a diagram illustrating an example of the CT image Bt1 of the brain. The CT image Bt1 is a three-dimensional image. However, here, for ease of understanding, the description will be made using a two-dimensional tomographic image in one tomographic plane of the CT image Bt1. For example, in the CT image Bt1 illustrated in FIG. 12, a region represented by an arrow indicates middle cerebral artery trunk occlusion and the classification thereof is MCA. As illustrated in FIG. 12, the learning unit 22-2 trains a discriminator 23-2 which discriminates an anatomic part of thrombus in the input CT image B0, using the correct information of an anatomic part of thrombus specified in the CT image Bt1 as training data.

Figure 13:
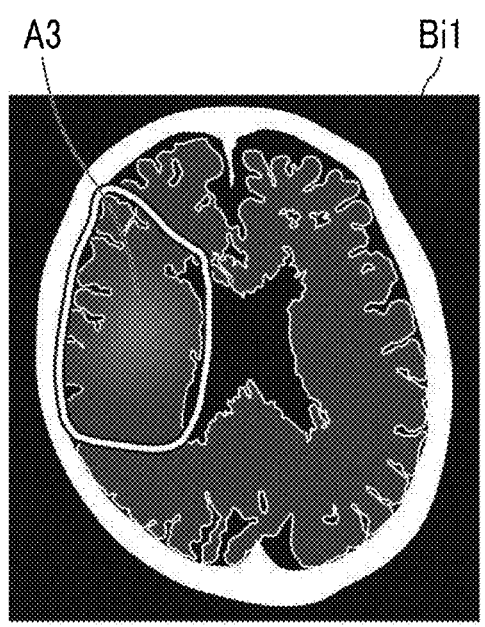
FIG. 13 is a diagram illustrating an example of the CT image of the brain.

FIG. 13 is a diagram illustrating an example of the CT image Bi1 of the brain. The CT image Bi1 is a three-dimensional image. However, here, for ease of understanding, the description will be made using a two-dimensional tomographic image in one tomographic plane of the CT image Bi1. As illustrated in FIG. 13, the CT image Bi1 includes the skull and the brain parenchyma. As illustrated in FIG. 13, the learning unit 22-2 trains the discriminator 23-2 which discriminates whether or not an infarction region is present in the input CT image B0, using a CT image Bi1 including an infarction region A3 as training data of information indicating that there is an infarction region and a CT image Bi1 without including the infarction region A3 as training data of information indicating that there is no infarction region.

Here, the discriminator 23-2 according to the second embodiment will be described. The discriminator 23-2 differs from the discriminator 23 according to the first embodiment in that it further comprises a fourth CNN 34 and a fifth CNN 35.

Figure 14:
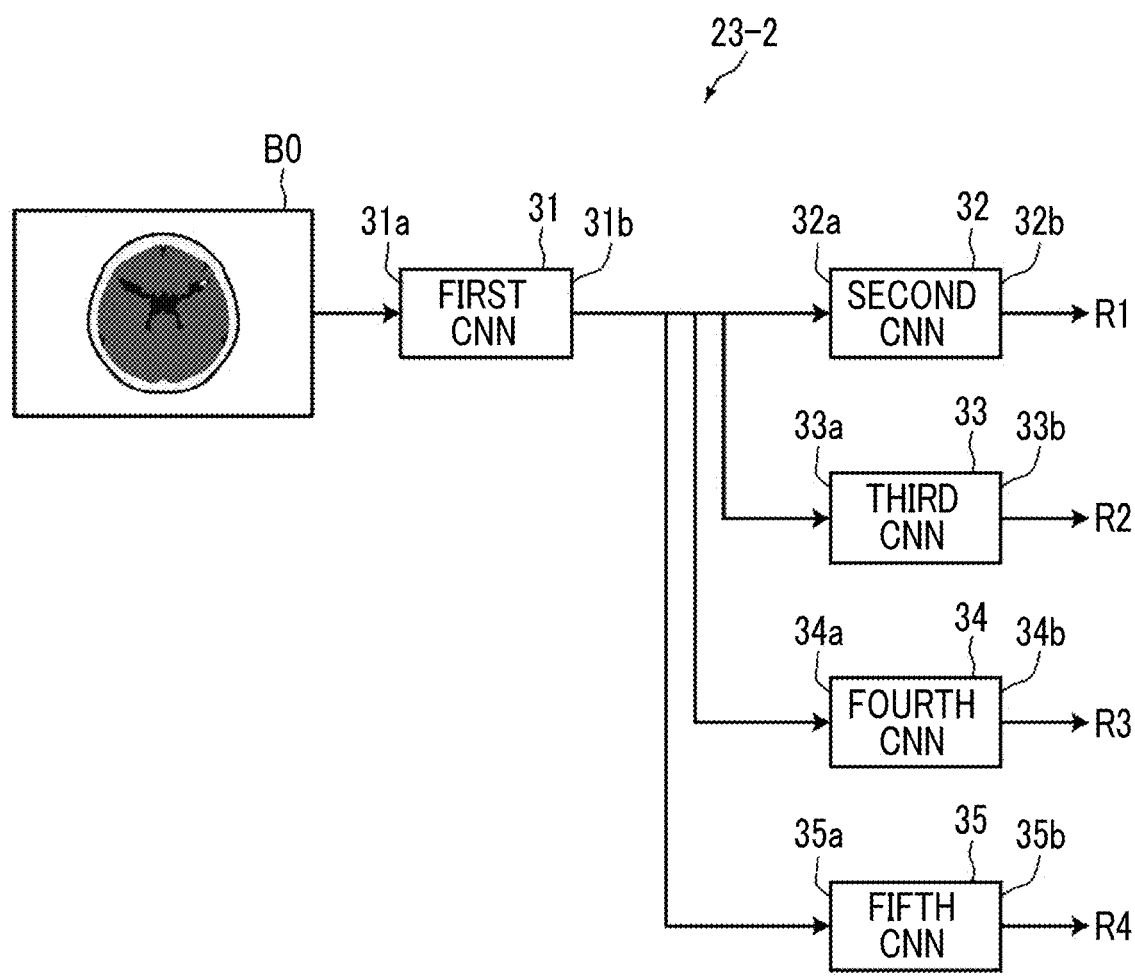
FIG. 14 is a diagram schematically illustrating the configuration of a discriminator in a second embodiment.

FIG. 14 is a diagram schematically illustrating the configuration of the discriminator 23-2 according to the second embodiment. As illustrated in FIG. 14, the discriminator 23-2 includes the first CNN 31, the second CNN 32, the third CNN 33, the fourth CNN 34, and the fifth CNN 35. The first CNN 31, the second CNN 32, the third CNN 33, the fourth CNN 34, and the fifth CNN 35 are configured to have a plurality of processing layers including input layers 31a, 32a, 33a, 34a, and 35a as input units and output layers 31b, 32b, 33b, 34b, and 35b as output units. The output layer 31b of the first CNN 31 is connected to the input layer 32a of the second CNN 32, the input layer 33a of the third CNN 33, the input layer 34a of the fourth CNN 34, and the input layer 35a of the fifth CNN 35. In addition, the fourth CNN 34 corresponds to a third learning unit according to the present disclosure and the fifth CNN 35 corresponds to a fourth learning unit according to the present disclosure.

The processing layers of the fourth CNN 34 and the fifth CNN 35 include at least one of a convolutional layer or a pooling layer, similarly to the processing layers of the first CNN 31, the second CNN 32, and the third CNN 33.

In this embodiment, the first CNN 31 and the fourth CNN 34 are trained, using the correct information of an anatomic part of thrombus specified in a plurality of CT images of the brain including a thrombus region as training data, so as to output a discrimination result R3 of an anatomic part for a thrombus region included in the input CT image. In a case in which the CT image B0 is input to the input layer 31a of the first CNN 31, among a plurality of processing layers of the first CNN 31 and the fourth CNN 34, a feature amount map output from a processing layer in the previous stage is sequentially input to a processing layer in the next stage and the discrimination result R3 of an anatomic part for the thrombus region included in the CT image B0 is output from the output layer 34b of the fourth CNN 34. In addition, the discrimination result R3 output from the fourth CNN 34 is the result of discriminating whether or not each anatomic part of the CT image B0 is a thrombus region.

The first CNN 31 and the fifth CNN 35 are trained, using information indicating whether or not a classified infarction region is present in the CT image Bi1 as training data, so as to output a result R4 of discriminating whether or not an infarction region is present in the input CT image. In a case in which the CT image B0 is input to the input layer 31a of the first CNN 31, among a plurality of processing layers of the first CNN 31 and the fifth CNN 35, a feature amount map output from a processing layer in the previous stage is sequentially input to a processing layer in the next stage and the result R4 of discriminating whether or not an infarction region is present in the CT image B0 is output from the output layer 35b of the fifth CNN 35. In addition, the discrimination result R4 output from the fifth CNN 35 is the result of discriminating whether or not an infarction region is present in the CT image B0.

Here, in the second embodiment, the feature amount map output from the output layer 31b of the first CNN 31 is input to all of the input layer 32a of the second CNN 32, the input layer 33a of the third CNN 33, the input layer 34a of the fourth CNN 34, and the input layer 35a of the fifth CNN 35. That is, the first CNN 31 outputs a common feature amount map in all of a case in which a thrombus region is discriminated, a case in which an infarction region is discriminated, a case in which an anatomic part of the thrombus region is discriminated, and a case in which it is discriminated whether or not an infarction region is present.

In the second embodiment, the first CNN 31 is trained using not only data indicating a correct thrombus region and data indicating a correct infarction region but also data indicating the correct information of an anatomic part of thrombus and data of information indicating whether or not an infarction region is present. That is, not only the knowledge of thrombus but also the knowledge of an anatomic part of the blood vessel of the brain and the knowledge of infarction are reflected in the discrimination result R1 of the thrombus region output from the second CNN 32. Therefore, the accuracy of the discrimination result is improved. Similarly, not only the knowledge of infarction but also the knowledge of thrombus and the knowledge of an anatomic part of the blood vessel of the brain are reflected in the discrimination result R2 of the infarction region output from the third CNN 33. Therefore, the accuracy of the discrimination result is improved.

Similarly, not only the knowledge of an anatomic part of the blood vessel of the brain but also the knowledge of thrombus and the knowledge of infarction are reflected in the discrimination result R3 of an anatomic part of the thrombus region output from the fourth CNN 34. Therefore, the accuracy of the discrimination result is improved. Similarly, not only whether or not an infarction region is present but also the knowledge of infarction, the knowledge of thrombus, and the knowledge of an anatomic part of the blood vessel of the brain are reflected in the result R4 of discriminating whether or not an infarction region is present which is output from the fifth CNN 35. Therefore, the accuracy of the discrimination result is improved.

Figure 15:
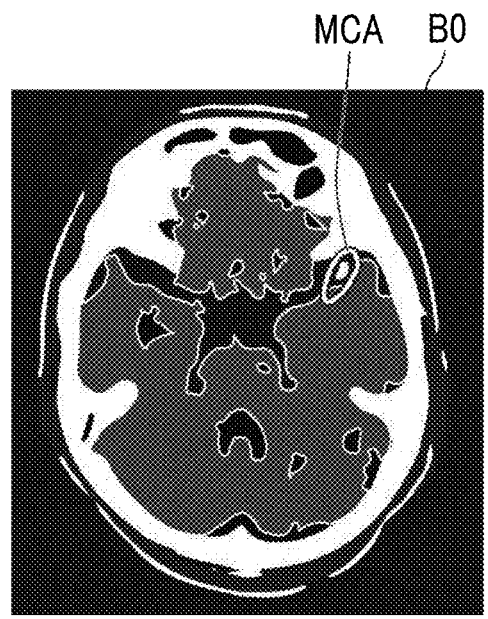
FIG. 15 is a diagram illustrating a displayed CT image of the brain.

In the second embodiment, the display control unit 24 displays the brain image in which an anatomic part of the thrombus region has been classified on the display unit 14. FIG. 15 is a diagram illustrating the displayed CT image of the brain. In addition, FIG. 15 illustrates a slice image in one tomographic plane of the CT image B0. As illustrated in FIG. 15, the display control unit 24 displays "MCA" as the anatomic part of the thrombus region classified in the CT image B0. In addition, the display control unit 24 may display the anatomic part of the thrombus region on the display unit 14 in any aspect as long as it can display the anatomic part of the thrombus region so as to be known. For example, the display control unit 24 may display a list of the anatomic parts such that a corresponding part is highlighted.

Figure 16:
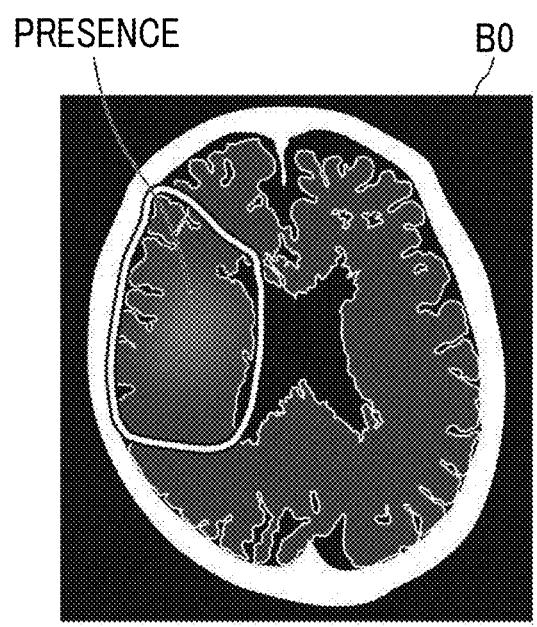
FIG. 16 is a diagram illustrating a displayed CT image of the brain.

Further, the display control unit 24 displays the brain image in which the presence and absence of an infarction region have been classified on the display unit 14. FIG. 16 is a diagram illustrating the displayed CT image of the brain. In addition, FIG. 16 illustrates a slice image in one tomographic plane of the CT image B0. As illustrated in FIG. 16, the display control unit 24 displays "presence" as information indicating whether or not a classified infarction region is present in the CT image B0. Further, the display control unit 24 may perform display in any aspect as long as it can perform display such that the presence and absence of an infarction region are known.

Next, a process performed in the second embodiment will be described. The flowchart illustrated in FIG. 8 can be used to describe the process performed during learning in the second embodiment. First, the image acquisition unit 21 acquires the CT images Bt1 and Bi1 of the brain of the subject that has developed cerebral thrombosis or cerebral infarction (Step ST1). Then, the learning unit 22 trains the discriminator 23-2 which discriminates a thrombus region, an infarction region, an anatomic part of thrombus, and whether or not an infarction region is present in the input CT image B0, using the thrombus region and the infarction region specified in the CT images Bt1 and Bi1, respectively, and information indicating an anatomic part of thrombus and information indicating whether or not an infarction region is present in the CT images Bt1 and Bi1 as training data (Step ST2). Then, the process ends.

Figure 17:
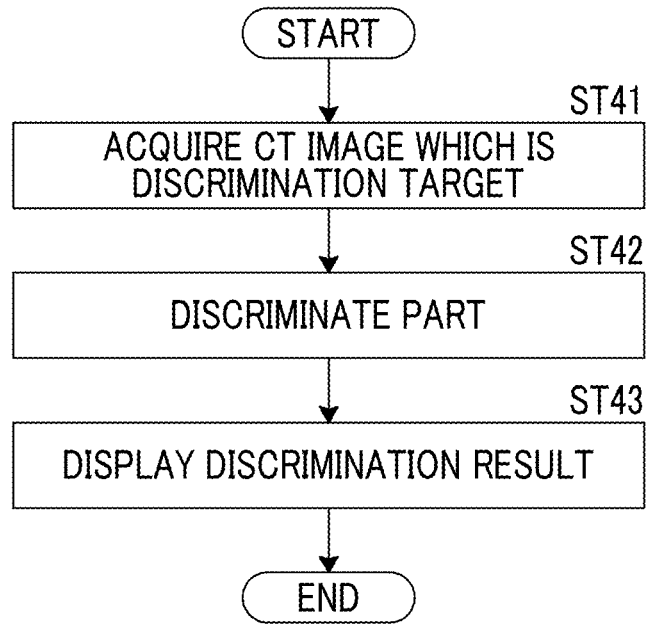
FIG. 17 is a flowchart illustrating a process performed during the discrimination of a part.

FIG. 17 is a flowchart illustrating a process performed during the discrimination of a part in the second embodiment. First, the image acquisition unit 21 acquires the CT image B0 which is a discrimination target (Step ST41) and the discriminator 23-2 discriminates an anatomic part of a thrombus region in the CT image B0 which is a discrimination target (Step ST42). Then, the display control unit 24 displays the CT image B0 in which the anatomic part has been discriminated on the display unit 14 (Step ST43). Then, the process ends.

Figure 18:
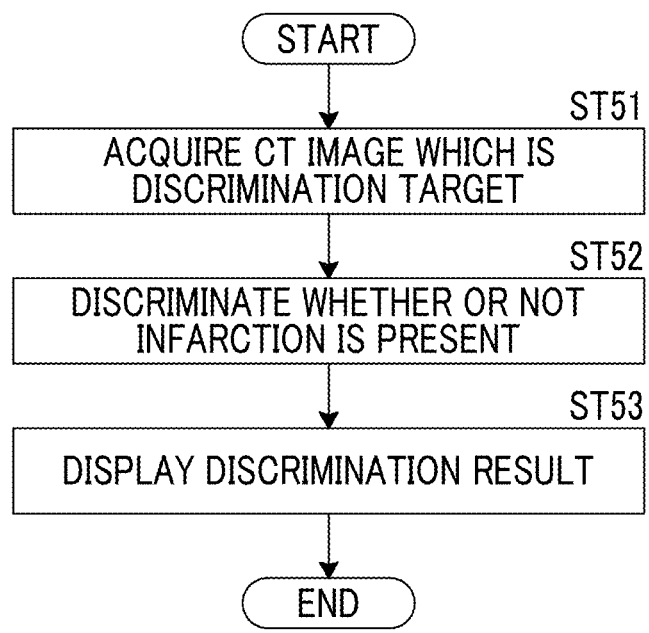
FIG. 18 is a flowchart illustrating a process performed in a case in which it is discriminated whether or not an infarction region is present.

FIG. 18 is a flowchart illustrating a process performed in a case in which it is discriminated whether or not an infarction region is present in the second embodiment. First, the image acquisition unit 21 acquires the CT image B0 which is a discrimination target (Step ST51) and the discriminator 23-2 discriminates whether or not an infarction region is present in the CT image B0 which is a discrimination target (Step ST52). Then, the display control unit 24 displays the CT image B0 in which the presence and absence of the infarction region have been discriminated on the display unit 14 (Step ST53). Then, the process ends.

As described above, in the second embodiment, not only the knowledge of thrombus but also the knowledge of an anatomic part of the blood vessel of the brain and the knowledge of infarction are reflected in the discrimination result of the thrombus region output from the second CNN 32. Not only the knowledge of infarction but also the knowledge of thrombus and the knowledge of an anatomic part of the blood vessel of the brain are reflected in the discrimination result of the infarction region output from the third CNN 33. Not only the knowledge of an anatomic part of the blood vessel of the brain but also the knowledge of infarction and the knowledge of thrombus are reflected in the discrimination result of an anatomic part for the thrombus region which is output from the fourth CNN 34. Not only the knowledge of the presence and absence of an infarction region but also the knowledge of infarction, the knowledge of thrombus, and the knowledge of an anatomic part of the blood vessel of the brain are reflected in the result of discriminating whether or not an infarction region is present which is output from the fifth CNN 35. As a result, the accuracy of the discrimination result is improved. Therefore, the discriminator 23-2 according to the second embodiment is trained using knowledge in a wider range than that in the first embodiment, which makes it possible to discriminate a disease region with high accuracy.

In addition, in the second embodiment, four CNNs 32, 33, 34, and 35 are provided as a plurality of learning units according to the present disclosure. However, the technology according to the present disclosure is not limited thereto and two or more CNNs may be provided.

In the above-described embodiments, the first disease is thrombus and the second disease is infarction. However, the technology according to the present disclosure is not limited thereto. The first disease may be infarction and the second disease may be thrombus. In addition, the first disease or the second disease may be, for example, bleeding.

In the above-described embodiments, the CT image is used as the brain image.

However, the technology according to the present disclosure is not limited thereto. Other medical images, such as MRI images and PET images, may be used.

In the above-described embodiments, the brain image is used as the medical image. However, the technology according to the present disclosure is not limited thereto. For example, the present disclosure may also be applied to a case in which medical characteristics included in the medical images of the chest, abdomen, whole body, and limbs of the human body are discriminated.

In the above-described embodiments, the convolutional neural network is used as each CNN. However, the technology according to the present disclosure is not limited thereto. For example, neural networks including a plurality of processing layers, such as a deep neural network (DNN) and a recurrent neural network (RNN) may be used. In addition, all neural networks may not be the same neural network. For example, the first CNN 31 may be a convolutional neural network and the other CNNs may be recurrent neural networks. The type of CNN may be appropriately changed.

In the above-described embodiments, the CNNs other than the first CNN 31 which is the common learning unit according to the present disclosure are not connected to each other. However, in the technology according to the present disclosure, the CNNs other than the first CNN 31 may be connected to each other.

In the above-described embodiments, the non-contrast-enhanced CT images are used as the CT images B0, Bt1, and Bi1. However, both the contrast-enhanced CT image and the non-contrast-enhanced CT image may be used to train the discriminators 23 and 23-2. As such, the use of the trained discriminators 23 and 23-2 makes it possible to discriminate a thrombus region and an infarction region even in a case in which the CT image which is an extraction target is either a contrast-enhanced CT image or a non-contrast-enhanced CT image.

In the above-described embodiments, for example, the following various processors can be used as the hardware structure of processing units performing various processes, such as the image acquisition unit 21, the learning unit 22, the discriminator 23, and the display control unit 24. The various processors include a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

EXPLANATION OF REFERENCES

1: disease region discrimination apparatus
2: three-dimensional imaging apparatus
3: image storage server
4: network
11: CPU
12: memory
13: storage
14: display unit
15: input unit
21: image acquisition unit
22, 22-2: learning unit
23, 23-2: discriminator
24: display control unit
31: first CNN (common learning unit)
32: second CNN (first learning unit)
33: third CNN (second learning unit)
34: fourth CNN (third learning unit)
35: fifth CNN (fourth learning unit)
A1: thrombus region
A2: infarction region
B0: CT image as discrimination target
Bt1: CT image including thrombus region
Bi1: CT image including infarction region

What is claimed is:

1. A learning method that trains a discriminator comprising a common convolutional neural network (CNN) that includes an input unit and an output unit and a plurality of CNNs each of which includes an input unit which is connected to the output unit of the common CNN and an output unit, the method comprising:

training the common CNN and a first CNN among the plurality of CNNs of the discriminator, using a plurality of data sets of a medical image and an image data of a first disease region in which a first disease appears in the medical image, such that information indicating the first disease region is output from the output unit of the first CNN among the plurality of CNNs in a case in which the medical image is input to the input unit of the common CNN; and training the common CNN and a second CNN among the plurality of CNNs of the discriminator, using a plurality of data sets of a medical image and an image data of a second disease region in which a second disease having at least one of a medical causal relationship or an anatomic causal relationship with the first disease appears in the medical image, such that information indicating the second disease region is output from the output unit of the second CNN among the plurality of CNNs in a case in which the medical image is input to the input unit of the common CNN, wherein after the discriminator being trained, the common CNN outputs a feature amount map common to a case in which the first disease is discriminated and a case in which the second disease is discriminated.

2. The learning method according to claim 1, wherein the common CNN is trained, using the plurality of data sets of a medical image and an image data of a first disease region in which the first disease appears in the medical image and the plurality of data sets of a medical image and an image data of a second disease region in which the second disease appears in the medical image, such that a feature amount data of the medical image is output from the output unit of the common CNN in a case in which the medical image is input to the input unit of the common CNN.

3. The learning method according to claim 2, wherein the discriminator is trained, using a plurality of data sets of a medical image and correct information of an anatomic part of the first disease in the medical image, such that information indicating the anatomic part of the first disease is output from the output unit of a third CNN among the plurality of CNNs in a case in which the medical image is input to the input unit of the common CNN.

4. The learning method according to claim 1, wherein the discriminator is trained, using a plurality of data sets of a medical image and correct information of an anatomic part of the first disease in the medical image, such that information indicating the anatomic part of the first disease is output from the output unit of a third CNN among the plurality of CNNs in a case in which the medical image is input to the input unit of the common CNN.

5. The learning method according to claim 1, wherein the discriminator is trained, using a plurality of data sets of a medical image and information indicating whether or not the second disease is present in the medical image, such that the information indicating whether or not the second disease is present is output from the output unit of a fourth CNN among the plurality of CNNs in a case in which the medical image is input to the input unit of the common CNN.

6. The learning method according to claim 1, wherein each of the common CNN and the plurality of CNNs is a neural network that comprises an input layer as the input unit, a plurality of intermediate layers, and an output layer as the output unit.

7. The learning method according to claim 1, wherein the first disease is thrombus and the second disease is infarction.

8. The learning method according to claim 1, wherein the medical image is a brain image.

9. A discriminator that is trained by the learning method according to claim 1.

10. A learning apparatus that trains a discriminator comprising a common CNN that includes an input unit and an output unit and a plurality of CNNs each of which includes an input unit which is connected to the output unit of the common CNN and an output unit, the learning apparatus configured to:
train the common CNN and a first CNN among the plurality of CNNs of the discriminator, using a plurality of data sets of a medical image and an image data of a first disease region in which a first disease appears in the medical image, such that information indicating the first disease region is output from the output unit of the first CNN among the plurality of CNNs in a case in which the medical image is input to the input unit of the common CNN; and
train the common CNN and a second CNN among the plurality of CNNs of the discriminator, using a plurality of data sets of a medical image and an image data of a second disease region in which a second disease having at least one of a medical causal relationship or an anatomic causal relationship with the first disease appears in the medical image, such that information indicating the second disease region is output from the output unit of the second CNN among the plurality of CNNs in a case in which the medical image is input to the input unit of the common CNN,
wherein after the discriminator being trained, the common CNN outputs a feature amount map common to a case in which the first disease is discriminated and a case in which the second disease is discriminated.

11. The learning apparatus according to claim 10, further configured to:
train the common CNN, using the plurality of data sets of a medical image and an image data of a first disease region in which the first disease appears in the medical image and the plurality of data sets of a medical image and an image data of a second disease region in which the second disease appears in the medical image, such that a feature amount data of the medical image is output from the output unit of the common CNN in a case in which the medical image is input to the input unit of the common CNN.

12. A discriminator that is trained by the learning apparatus according to claim 10.

13. A non-transitory computer readable medium for storing a learning program that trains a discriminator comprising a common CNN that includes an input unit and an output unit and a plurality of CNNs each of which includes an input unit which is connected to the output unit of the common CNN and an output unit, the learning program causing a computer to perform:
a process of training the common CNN and a first CNN among the plurality of CNNs of the discriminator, using a plurality of data sets of a medical image and an image data of a first disease region in which a first disease appears in the medical image, such that information indicating the first disease region is output from the output unit of the first CNN among the plurality of CNNs in a case in which the medical image is input to the input unit of the common CNN; and
a process the common CNN and a second CNN among the plurality of CNNs of training the discriminator, using a plurality of data sets of a medical image and an image data of a second disease region in which a second disease having at least one of a medical causal relationship or an anatomic causal relationship with the first disease appears in the medical image, such that information indicating the second disease region is output from the output unit of the second CNN among the plurality of CNNs in a case in which the medical image is input to the input unit of the common CNN,
wherein after the discriminator being trained, the common CNN outputs a feature amount map common to a case in which the first disease is discriminated and which the second disease is discriminated.

14. A non-transitory computer readable medium for storing a learning program according to claim 13, the learning program further causing a computer to perform:
a process of training the common CNN, using the plurality of data sets of a medical image and an image data of a first disease region in which the first disease appears in the medical image and the plurality of data sets of a medical image and an image data of a second disease region in which the second disease appears in the medical image, such that a feature amount data of the medical image is output from the output unit of the common CNN in a case in which the medical image is input to the input unit of the common CNN.

15. A discriminator that is trained by the learning program according to claim 13.

16. A disease region discrimination apparatus comprising:
an image acquisition unit that acquires a medical image which is a discrimination target; and
the discriminator according to claim 9 that discriminates a first disease region in the medical image which is the discrimination target.

17. The disease region discrimination apparatus according to claim 16, further comprising:

a display control unit that displays a discrimination result of the discriminator on a display unit.

18. A disease region discrimination apparatus comprising:

an image acquisition unit that acquires a medical image which is a discrimination target; and the discriminator according to claim 16 that discriminates a second disease region in the medical image which is the discrimination target.

19. A non-transitory computer readable medium for storing a disease region discrimination program that causes a computer to perform:

a process of acquiring a medical image which is a discrimination target; and a process of allowing the discriminator according to claim 9 to discriminate a first disease region in the medical image which is the discrimination target.

20. A non-transitory computer readable medium for storing a disease region discrimination program that causes a computer to perform:

a process of acquiring a medical image which is a discrimination target; and a process of allowing the discriminator according to claim 9 to discriminate a second disease region in the medical image which is the discrimination target.

* * * * *